United States Patent
Lee et al.

(10) Patent No.: US 10,112,122 B2
(45) Date of Patent: Oct. 30, 2018

(54) DEVICE FOR PREPARING ALKANOL (71) Applicant: LG CHEM, LTD., Seoul (KR)

(72) Inventors: Sung Kyu Lee, Daejeon (KR); Joon Ho Shin, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 535 days.

(21) Appl. No.: 14/443,591

(22) PCT Filed: Jan. 16, 2014

(86) PCT No.: PCT/KR2014/000480
§ 371 (c)(1),
(2) Date: May 18, 2015

(87) PCT Pub. No.: WO2014/112808
PCT Pub. Date: Jul. 24, 2014

(65) Prior Publication Data
US 2015/0306517 A1    Oct. 29, 2015

(30) Foreign Application Priority Data

Jan. 16, 2013  (KR) .................. 10-2013-0004943
Jan. 16, 2014  (KR) .................. 10-2014-0005491

(51) Int. Cl.
*B01D 3/14* (2006.01)
*C07C 31/04* (2006.01)
(Continued)

(52) U.S. Cl.
CPC ............. *B01D 3/141* (2013.01); *B01J 19/24* (2013.01); *C07C 29/80* (2013.01); *C07C 31/04* (2013.01)

(58) Field of Classification Search
CPC .......................... B01D 3/141; B01D 2259/65
See application file for complete search history.

(56) References Cited

U.S. PATENT DOCUMENTS 6,117,277 A    9/2000  Zgorzelski et al.
7,594,981 B2 *  9/2009  Ikeda .................. B01D 3/14
                                                    203/18
(Continued)

FOREIGN PATENT DOCUMENTS

CN   102190559 A   9/2011
CN   102355929 A   2/2012
(Continued)

OTHER PUBLICATIONS

"Pinch Analysis: Part 1." Separation Technologies, Mar. 21, 2012, seperationtechnology.com/pinch-analysis-part-1/. (Year: 2012).*
(Continued)

*Primary Examiner* — Bobby Ramdhanie
*Assistant Examiner* — Briana M Obenhuber
(74) *Attorney, Agent, or Firm* — Dentons US LLP (57) ABSTRACT

The present application relates to a device and a method for preparing alkanol. According to the present application, energy can be reduced when preparing alkanol by reducing the amount of steam used in a reboiler or cooling water used in a condenser and a cooler, and steam generated from a heat exchanger for column top stream can be utilized in a variety of fields. Also, highly pure alkanol can be prepared according to the present application.

16 Claims, 8 Drawing Sheets

(51) Int. Cl.
   *B01J 19/24* (2006.01)
   *C07C 29/80* (2006.01)

(56) References Cited

U.S. PATENT DOCUMENTS

| | | | | |
|---|---|---|---|---|
| 8,932,434 | B2* | 1/2015 | Lee | B01D 3/14 202/158 |
| 9,511,306 | B2 | 12/2016 | Lee et al. | |
| 2002/0023830 | A1* | 2/2002 | Tamura | B01D 3/14 203/74 |
| 2003/0139631 | A1 | 7/2003 | Muller et al. | |
| 2012/0004473 | A1* | 1/2012 | Lee | B01D 3/141 568/913 |
| 2012/0006673 | A1 | 1/2012 | Lee et al. | |
| 2013/0334029 | A1 | 12/2013 | Lee et al. | |
| 2015/0041308 | A1 | 2/2015 | Lee et al. | |

FOREIGN PATENT DOCUMENTS

| | | | |
|---|---|---|---|
| EP | 2045232 A1 | 4/2009 | |
| EP | 2409746 A2 | 1/2012 | |
| JP | 46-34018 B | 10/1971 | |
| JP | 58-55002 A | 4/1983 | |
| JP | 09-299702 A | 11/1997 | |
| JP | 2000-140501 A | 5/2000 | |
| JP | 2000-334201 A | 12/2000 | |
| JP | 2010-540582 A | 12/2010 | |
| JP | 2011-162502 A | 8/2011 | |
| JP | 2012-515771 A | 7/2012 | |
| JP | 2012-520874 A | 9/2012 | |
| KR | 100410705 | 3/2004 | |
| KR | 1020070025556 | 3/2007 | |
| KR | 10-0804821 B1 | 2/2008 | |
| KR | 1020100105500 | 9/2010 | |
| WO | 2004/073841 A1 | 9/2004 | |
| WO | 2009/048335 A1 | 4/2009 | |
| WO | 2010/107283 A2 | 9/2010 | |
| WO | WO 2010107284 A2 * | 9/2010 | B01D 3/14 |

OTHER PUBLICATIONS

"Pinch Analysis: Part 2." Separation Technologies, Apr. 12, 2012, seperationtechnology.com/pinch-analysis-part-1/. (Year: 2012).*
Sandev, Mukesh. "Pinch Technology: Basics for Beginners." Cheresources.com Community, The Chemical Engineers Resource Page, Nov. 8, 2010, www.cheresources.com/content/articles/heat-transfer/pinch-technology-basics-for-beginners, http://pages.mtu.edu/~jwsuther/erdm/pinchtech.pdf (Year: 2010).*

* cited by examiner

DEVICE FOR PREPARING ALKANOL

This application is a National Stage Application of International Application No. PCT/KR2014/000480, filed on Jan. 16, 2014, and claims the benefit of Korean Patent Application No. 10-2013-0004943, filed on Jan. 16, 2013, and Korean Patent Application No. 10-2014-0005491, filed on Jan. 16, 2014, all of which are hereby incorporated by reference in their entirety for all purposes as if fully set forth herein.

DESCRIPTION

Technical Field

The present application relates to a device and a method for preparing an alkanol.

Background Art

Alkanols such as octanols have been used for various applications in the chemical industry including, for example, perfumes, solvents for organic synthetic products, plasticizers, etc.

For example, octanols may be manufactured by hydrogenating n-butylaldehyde. In the foregoing, the octanols manufactured by means of a hydrogenation reaction may be distilled through at least one distillation column. Thereafter, some or all of a stream may pass through a reboiler or a condenser during a distillation process to reflux the stream to the distillation column, thereby obtain high-purity octanols.

DISCLOSURE

Technical Problem

The present application is directed to providing a device and a method for preparing an alkanol.

TECHNICAL SOLUTION

One aspect of the present application provides a device for preparing an alkanol. The exemplary preparing device may include a distillation column. For example, the preparing device may be a distillation column assembly or a distillation system including the distillation column. When the device for preparing an alkanol is used, a high-purity alkanol may be separated and refined while minimizing the loss of energy caused during a process of preparing an alkanol. Hereinafter, the device will be described with reference to the accompanying drawings. However, it should be understood that the drawings are shown herein for illustration only, and are not construed as limiting the scope of the device according to one exemplary embodiment of the present application.

Figure 1:
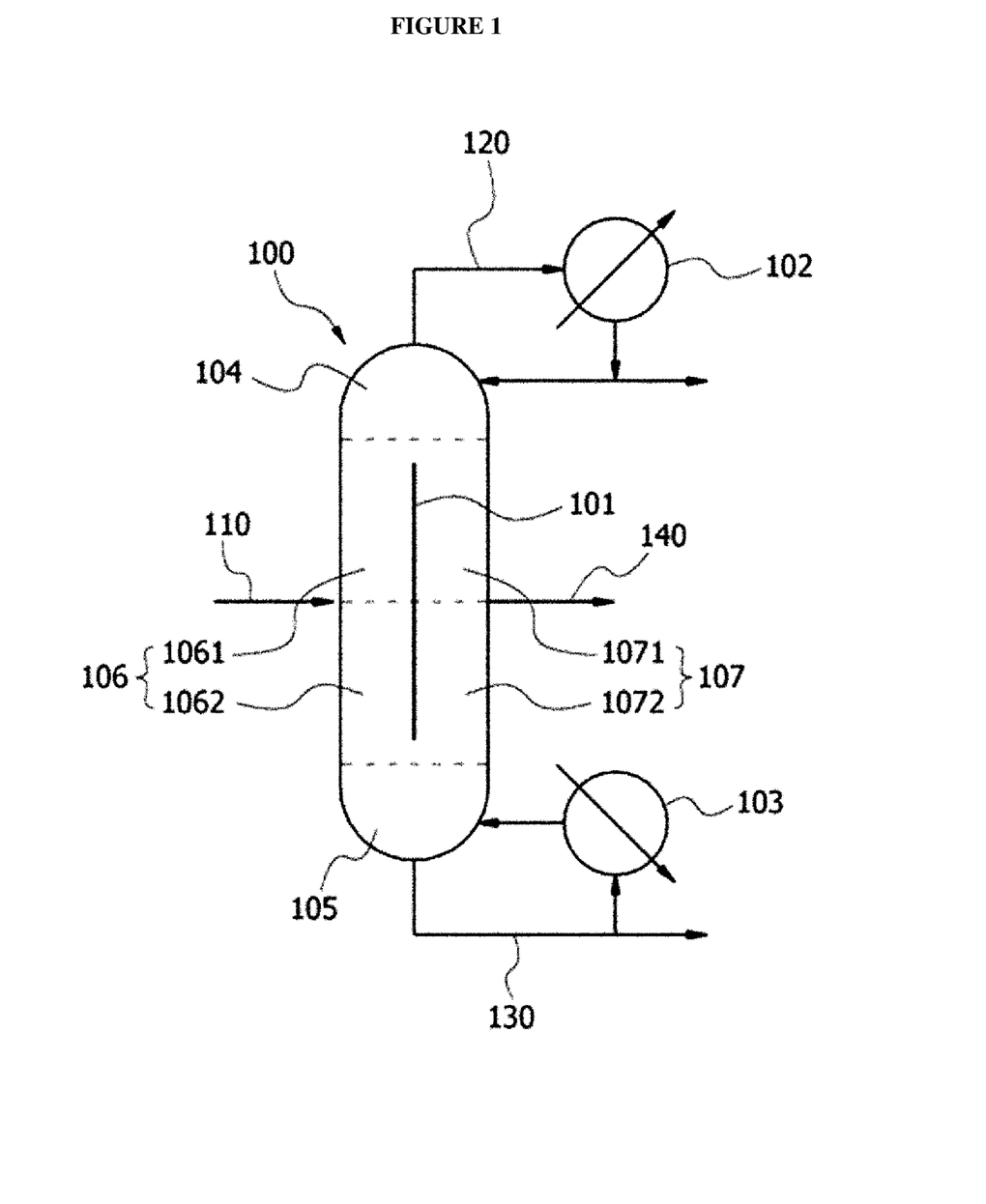
FIG. 1 is a diagram showing an exemplary divided-wall distillation column.

FIG. 1 is an exemplary diagram showing a device for preparing an alkanol. A device including a distillation column 100 into which a raw material 110 including a compound represented by the following Formula 1 flows is provided.

[Formula 1]

In Formula 1, R represents an alkyl group, for example, an alkyl group having 1 to 20 carbon atoms, 1 to 16 carbon atoms, 1 to 12 carbon atoms, or 1 to 8 carbon atoms. The alkyl group may have a linear, branched, or cyclic structure, and may be optionally substituted with one or more substituents, when necessary.

According to one exemplary embodiment, the component of Formula 1 may be an octanol, for example, 2-ethylhexanol.

In the foregoing, the distillation column 100 may be a divided-wall distillation column 100. The divided-wall distillation column 100 is generally a device designed to distill the raw material 110 including three components having a low boiling point, a middle boiling point, and a high boiling point. The divided-wall distillation column 100 is generally a device similar to a Petlyuk distillation column in a thermodynamic aspect. The Petlyuk distillation column has a structure in which a pre-fractionator and a main column are thermally integrated. The distillation column is designed so that a low boiling point material and a high boiling point material can be primarily separated at the pre-fractionator, components present in column top and column bottom regions of the pre-fractionator can flow into a feed stage of the main column, and the low boiling point material, the middle boiling point material and the high boiling point material can be separated at the main column. In this case, the divided-wall distillation column 100 is configured to install a divided wall 101 in the column so as to integrate the pre-fractionator into the main column.

The divided-wall distillation column 100 may, for example, have a structure as shown in FIG. 1. FIG. 1 shows an exemplary divided-wall distillation column 100. As shown in FIG. 1, the exemplary distillation column 100 may have a structure in which an inner part of the distillation column 100 is divided by a divided wall 101 and which has a condenser 102 and a reboiler 103 formed respectively in upper and lower portions thereof. Also, the inner part of the divided-wall distillation column 100 may be imaginarily divided by dotted lines shown in FIG. 1, for example, divided into a column top region 104 from which a low boiling point stream is discharged, a column bottom region 105 from which a high boiling point stream is discharged, a raw material feed region 106 in which a raw material 110 flows, and a product outflow region 107 from which a product flows out. Also, the raw material feed region 106 may be divided into an upper feed region 1061 and a lower feed region 1062, and the product outflow region 107 may be divided into an upper outflow region 1071 and a lower outflow region 1072. In the foregoing, the term "upper and lower feed regions" may refer to upper and lower regions, respectively, when the raw material feed region 106, that is, a space in a side of the divided-wall distillation column 100 in which the raw material 110 is fed in spaces divided by the divided wall 101 in the structure of the divided-wall distillation column 100, is bisected in a longitudinal direction of the distillation column 100. Also, the term "upper and lower outflow regions" may refer to upper and lower regions, respectively, when the product outflow region 107, that is, a space in a side of the divided-wall distillation column 100 from which a product flows out in the spaces divided by the divided wall 101 in the inner part of the divided-wall distillation column 100.

Specific types of the divided-wall distillation column 100 that may be used in a process of distilling an alkanol are not particularly limited. For example, the divided-wall distillation column 100 having a typical structure as shown in FIG. 1 may be used, or a distillation column in which the position and shape of the divided wall 101 in the distillation column are designed to be altered may also be used in consideration of refining efficiency. Also, the plate number and internal diameter of the distillation column are not particularly limited, and may, for example, determined based on a theoretical plate number derived from a distillation curve plotted in consideration of compositions of the raw material 110.

To perform a refining process on the raw material 110 including three components having a low boiling point, a middle boiling point, and a high boiling point, the raw material 110 may be introduced into the raw material feed region 106 of the divided-wall distillation column 100, as shown in FIG. 1. In the foregoing, the raw material 110 introduced into the raw material feed region 106 may be separated into a product stream 140, a column bottom stream 130, and a column top stream 120 to flow out therefrom. For example, after the raw material 110 flows into the raw material feed region 106 of the divided-wall distillation column 100, the column top stream 120 that is a component having a relatively low boiling point in the components of the raw material 110 is discharged from the column top region 104 of the divided-wall distillation column 100, and the column bottom stream 130 having a relatively high boiling point in the components of the raw material 110 is discharged from the column bottom region 105 of the divided-wall distillation column 100. Also, the component having a middle boiling point may be discharged as the product stream 140 from the product outflow region 107. According to one exemplary embodiment, when the raw material 110 including an octanol, for example 2-ethylhexanol, flows into the divided-wall distillation column 100, a low boiling point stream that is a component having a relatively low boiling point in components of the raw material 110 is discharged from the column top region 104 of the divided-wall distillation column 100, and a high boiling point stream that is a component having a relatively high boiling point in the components of the raw material 110 is separated and discharged from the column bottom region 105 of the divided-wall distillation column 100. Also, the product stream 140 including an octanol, such as 2-ethylhexanol, which is a component having a relatively middle boiling point in the components of the raw material 110 may be discharged from the product outflow region 107, for example, an upper outflow region 1071 or a lower outflow region 1072, of the divided-wall distillation column 100. After the column top stream 120 in the divided-wall distillation column 100 passes through the condenser 102 as described above, and some of the column top stream 120 may be refluxed to the column top region 104 of the distillation column, and the rest of the column top stream 120 may be stored as a product. Also, after the high boiling point stream in the divided-wall distillation column 100 passes through the reboiler 103, some of the high boiling point stream may be refluxed to the column bottom region 105 of the distillation column, and the rest of the high boiling point stream may be produced as a product. In the foregoing, the term "low boiling point stream" refers to a stream in which the low boiling point component having a relatively low boiling point discharged from the column top region 104 of the divided-wall distillation column 100 is rich, and the term "high boiling point stream" refers to a stream in which the high boiling point component having a relatively high boiling point discharged from the column bottom region 105 of the divided-wall distillation column 100 is rich. Also, the term "product stream" refers to a product flowing out from the product outflow region 107 of the divided-wall distillation column 100, that is, a stream in which the middle boiling point component is rich. In the foregoing, the term "rich stream" refers to a stream in which the low boiling point component included in the stream discharged from the column top region 104, the high boiling point component included in the stream discharged from the column bottom region 105, and the middle boiling point component included in the stream discharged from the product outflow region 107 have higher contents than the low boiling point component, the high boiling point component and the middle boiling point component included in the raw material 110, respectively. For example, the rich stream may refer to a stream in which each of the low boiling point component, the high boiling point component, and the low boiling point component included in the stream discharged from the column top region 104, the column bottom region 105, and the product outflow region 107 has a content of 50% by weight or more, 80% by weight or more, 90% by weight or more, 95% by weight or more, or 99% by weight or more. In this specification, the low boiling point stream and the column top stream 120 may be used synonymously, the high boiling point stream and the column bottom stream 130 may be used synonymously, and the middle boiling point stream and the product stream 140 may be used synonymously.

According to one exemplary embodiment of the present application, the preparing device may include a heat exchanger.

In the heat exchanger, some or all of at least one stream selected from the group consisting of the column top stream 120, the column bottom stream 130, and the product stream 140 may exchange heat. Therefore, a high-purity alkanol may be separated and refined while minimizing the loss of energy caused during a process of preparing an alkanol, for example, 2-ethylhexanol. According to one exemplary embodiment, in the heat exchanger, some or all of the column top stream 120 may exchange heat with water, or some or all of at least one stream selected from the group consisting of the column top stream 120, the column bottom stream 130, and the product stream 140 may exchange heat with the raw material 110 flowing into the raw material feed region 106.

Figure 2:
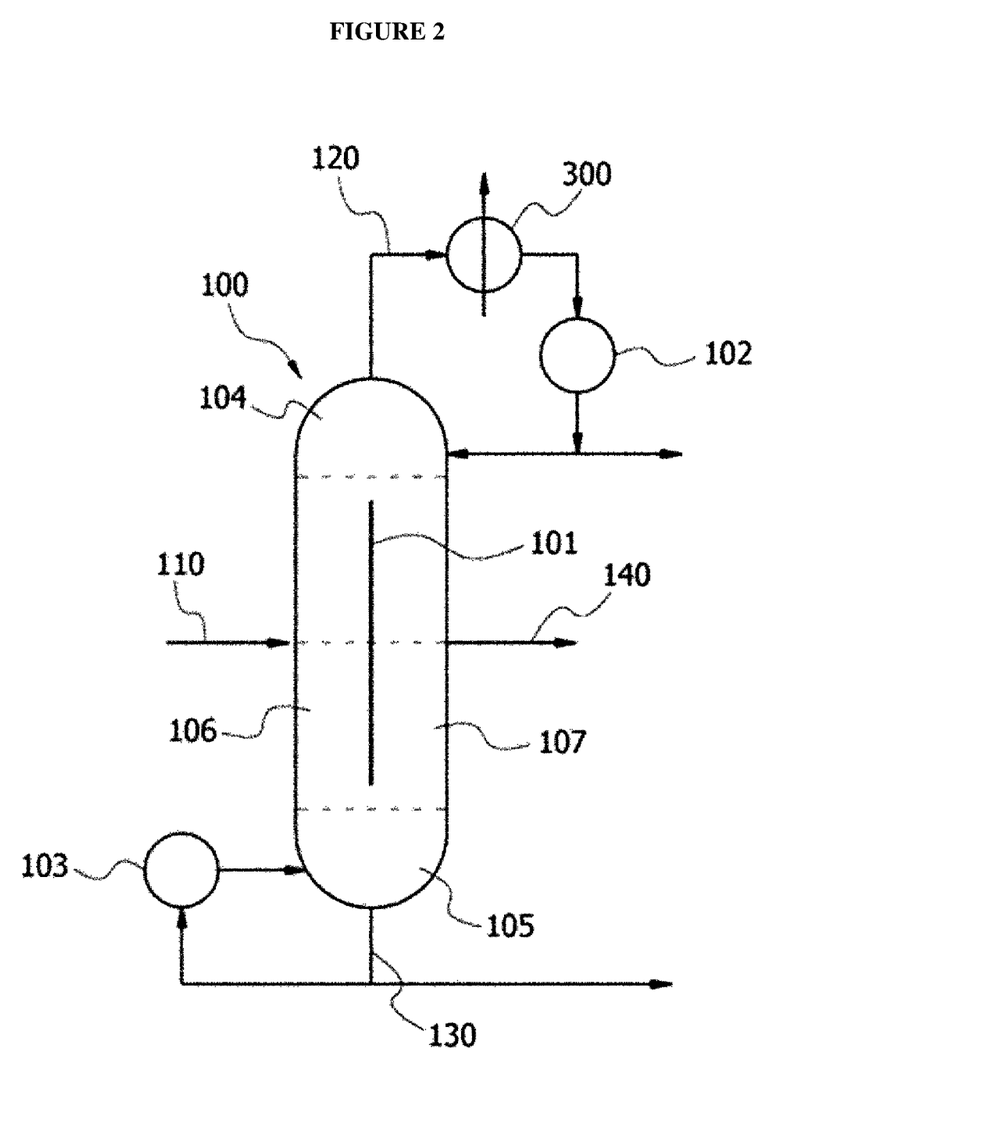
FIGS. 2 to 7 are diagrams showing exemplary embodiments of an exemplary device for preparing an alkanol.

FIG. 2 is a diagram showing a device for preparing an alkanol according to a first exemplary embodiment of the present application.

According to one exemplary embodiment, the heat exchanger may be a heat exchanger 300 for column top stream, as shown in FIG. 2. In the foregoing, the heat exchanger 300 for column top stream may be arranged to be directly or indirectly coupled to a pipe through which the low boiling point stream in the preparing device flows. In a thermodynamic aspect, the heat exchanger 300 for column top stream may be preferably directly coupled to the pipe through which the low boiling point stream in the distillation column 100 flows. Also, the heat exchanger 300 for column top stream may, for example, be arranged in a front stage of the condenser 102 so that the column top stream 120 sequentially passes through the heat exchanger 300 and the condenser 102. For example, after the low boiling point stream sequentially passes through the heat exchanger 300 for column top stream, and the condenser 102, some of the low boiling point stream passing through the condenser 102 may be refluxed to the distillation column 100.

Since the preparing device further include a heat exchanger 300 for column top stream as described above, the low boiling point stream in the divided-wall distillation column 100 passes through the heat exchanger 300 for column top stream. In this case, heat is applied to the heat exchanger 300 for column top stream. Therefore, the low boiling point stream is refluxed to the divided-wall distillation column 100 at a relatively low temperature. In this case, the cost spent in a condensation process in which the condenser 102 is used may be cut by reducing the quantity of energy used in the condensation process before the low boiling point stream is refluxed to the divided-wall distillation column 100.

According to one exemplary embodiment, the heat exchanger 300 for column top stream may be a heat exchanger configured to produce steam. In the exemplary preparing device, as the low boiling point stream passes through the heat exchanger 300 configured to produce steam for column top stream, in the heat exchanger 300 for column top stream, some or all of the low boiling point stream flowing out from the column top region 104 may exchange heat with water so as to produce high-temperature steam. The high-temperature steam produced in the heat exchanger 300 may, for example, used as a heat source in a vaporizer, a stripping column, or an isomer column used in a process of preparing an octanol. In this case, the low boiling point stream refluxed to the distillation column 100 after the heat exchange is completed may have a reflux ratio of 1 to 100. In a thermodynamic aspect, the reflux ratio of the low boiling point stream may be preferably in a range of 5 to 70, more preferably 18.5 to 25.5. When the reflux ratio of the low boiling point stream is adjusted in a range of 100 or less, preferably 70 or less, and most preferably 25.5 or less, as described above, the energy consumed to reflux the column top stream refluxed to the distillation column 100 in the column top stream 120 which has a temperature of 100 to 120° C. and is heat-exchanged with water by means of the heat exchanger 300 for column top stream may be minimized, and some of the column top stream 120 may be produced as a high-purity product at the same time. In this case, 2-ethylhexanol having a high purity, for example, a purity of 99.0% or more, may also be produced from the product stream by adjusting the reflux ratio in a range of 5 to 70, preferably 18 to 25.5. The term "reflux ratio" used herein refers to a ratio of a flow rate of a refluxed stream with respect to an outflow rate of a stream flowing out from the distillation column 100.

Figure 3:
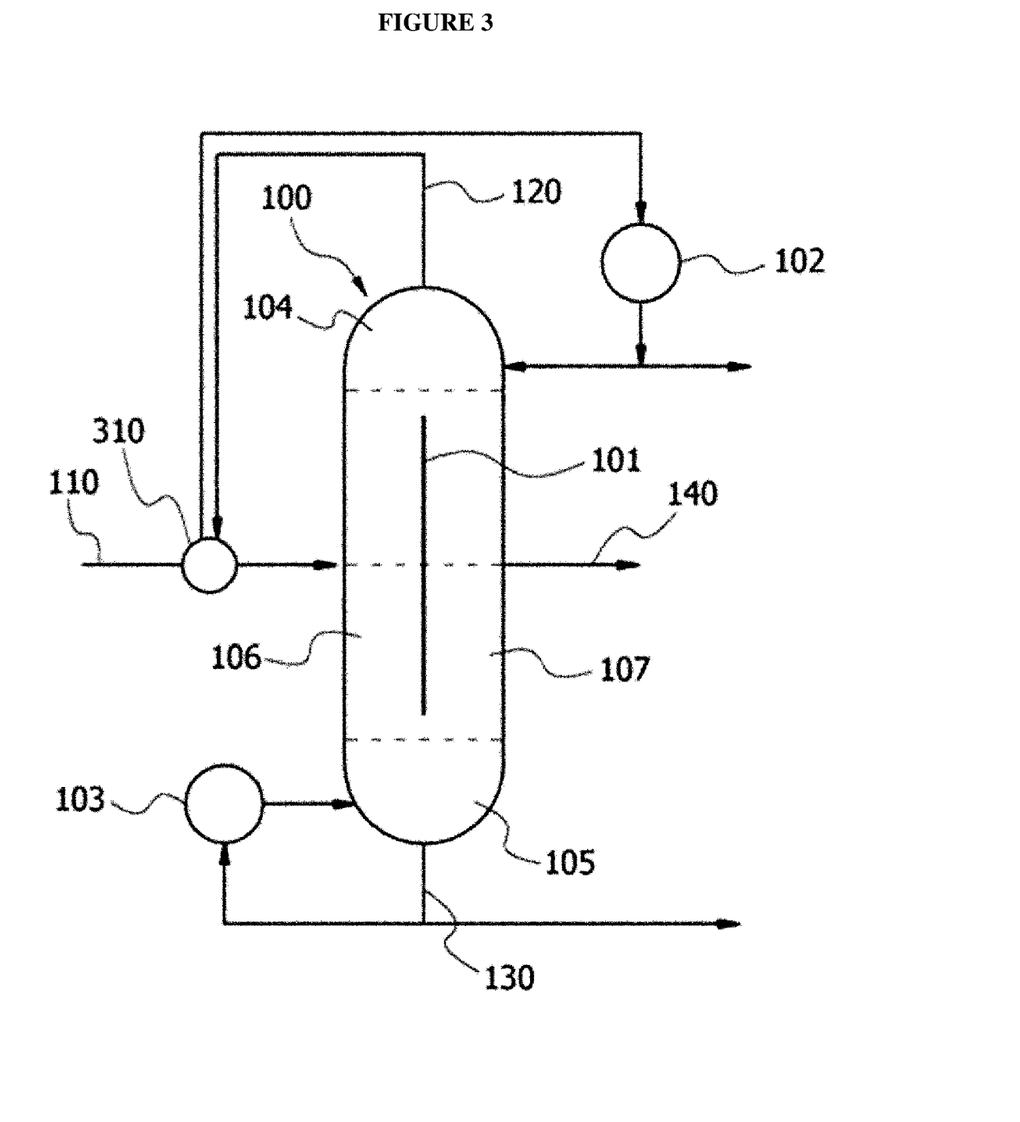

FIG. 3 is a diagram showing an exemplary preparing device according to a second exemplary embodiment of the present application.

As shown in FIG. 3, a heat exchanger 310 for column top stream may be a heat exchanger configured to preheat a raw material. In the exemplary preparing device, as the low boiling point stream passes through the heat exchanger 310 configured to preheat a raw material for column top stream, some or all of the low boiling point stream flowing out from the column top region 104 may exchange heat with the raw material 110 flowing into the raw material feed region 106 so as to preheat the raw material 110. As described above, the raw material 110 flowing into the divided-wall distillation column 100 may be preheated when the low boiling point stream exchanges heat with the raw material 110 flowing into the low-temperature divided-wall distillation column 100. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a condensation process in which the condenser 102 is used may be cut by reducing the quantity of cooling water used in the condensation process before the low boiling point stream in the divided-wall distillation column 100 is refluxed to the column top region 104 of the divided-wall distillation column 100. In this case, the low boiling point stream refluxed to the distillation column 100 after the heat exchange is completed may have a reflux ratio of 1 to 100. In a thermodynamic aspect, the reflux ratio of the low boiling point stream may be preferably in a range of 5 to 70, more preferably 8.4 to 17.3. When the reflux ratio of the low boiling point stream is adjusted in a range of 100 or less, preferably 70 or less, and most preferably 17.3 or less, as described above, the energy consumed to reflux the column top stream refluxed to the distillation column 100 in the column top stream 120 which has a temperature of 90 to 100° C. and is heat-exchanged with the raw material by means of the heat exchanger 300 for column top stream may be minimized, and some of the column top stream 120 may be produced as a high-purity product at the same time. In this case, 2-ethylhexanol having a high purity, for example, a purity of 99.0% or more, may also be produced from the product stream by adjusting the reflux ratio in a range of 5 to 70, preferably 8.4 to 17.3.

According to still another exemplary embodiment of the present application, the heat exchanger may be a heat exchanger for product stream, and, according to one exemplary embodiment, may be a heat exchanger configured to preheat a raw material.

Figure 4:
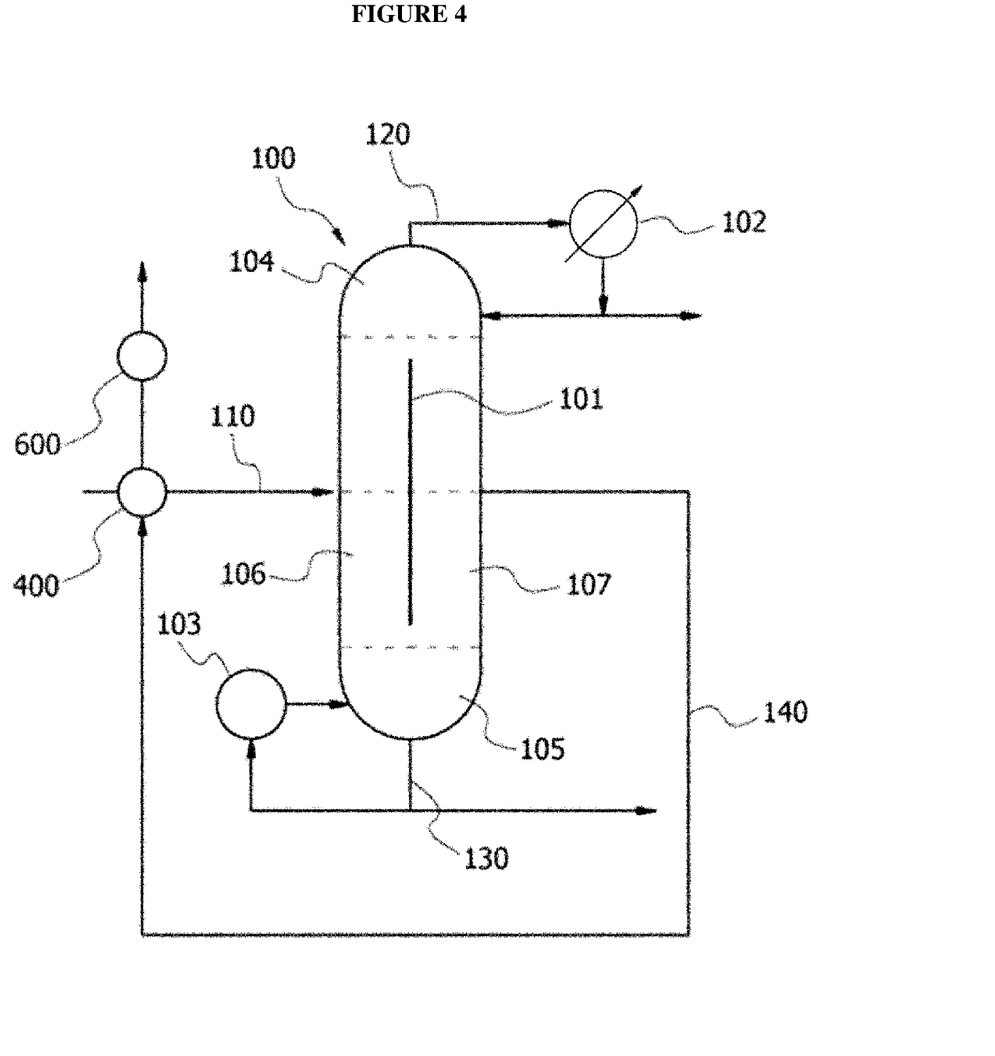

FIG. 4 is a diagram showing an exemplary preparing device according to a third exemplary embodiment of the present application.

As shown in FIG. 4, in the exemplary preparing device, as the product stream 140 including the middle boiling point stream passes through a heat exchanger 400 configured to preheat a raw material for product stream, some or all of the middle boiling point stream flowing out from the product outflow region 107 may exchange heat with the raw material 110 flowing out from the raw material feed region 106 so as to preheat the raw material 110. For example, as the product stream 140 flowing out from the product outflow region 107 of the divided-wall distillation column 100 passes through the heat exchanger 400 for product stream, in the heat exchanger 400 for product stream, some or all of the product stream 140 flowing out from the product outflow region 107 may exchange heat with the raw material 110 flowing into the raw material feed region 106 so as to preheat the raw material 110. By means of the heat exchanger 400 for product stream, the high-temperature product stream 140 discharged from the product outflow region 107 of the divided-wall distillation column 100 may flow through the pipe so that the product stream 140 can exchange heat with the raw material 110 flowing into the divided-wall distillation column 100 in the heat exchanger 400 for product stream, and then the product stream 140 may be produced as a product while sequentially passing through a cooler 600. As described above, the raw material 110 flowing into the divided-wall distillation column 100 may be preheated when the product stream 140 exchanges heat with the raw material 110 flowing into the low-temperature divided-wall distillation column 100. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a cooling process in which the cooler 600 is used may be cut by reducing the quantity of cooling water used in the cooling process before the stream including the octanol is produced as a product. In this case, the low boiling point stream refluxed to the distillation column 100 after the heat exchange is completed, that is, the column top stream, may have a reflux ratio of 1 to 100. In a thermodynamic aspect, the reflux ratio of the column top stream may be preferably in a range of 5 to 70, more preferably 15.2 to 18.5. When the reflux ratio of the column top stream is adjusted in a range of 100 or less, preferably 70 or less, and most preferably 18.5 or less, as described above, the energy consumed to cool the product stream 140 flowing into a storage tank in the column top stream 120 which has a temperature of 40 to 100° C. and is heat-exchanged with the raw material by means of the heat exchanger 400 for product stream may be minimized, and some of the column top stream 120 may be produced as a high-purity product at the same time. In this case, 2-ethylhexanol having a high purity, for example, a purity of 99.0% or more, may also be produced from the product stream 140 by adjusting the reflux ratio in a range of 5 to 70, preferably 15.2 to 18.5.

According to one exemplary embodiment, the preparing device may include both of the heat exchanger 300 for column top stream and the heat exchanger 400 for product stream. For example, when the preparing device includes both of the heat exchanger 300 for column top stream and the heat exchanger 400 for product stream, the heat exchanger 300 for column top stream may be a heat exchanger configured to produce steam. For example, as described above, as some or all of the low boiling point stream in the divided-wall distillation column 100, that is, the column top stream 120, passes through the heat exchanger 300 configured to produce steam for column top stream, the column top stream 120 may exchange heat with water to produce steam. For example, the steam produced in the heat exchanger 300 configured to produce steam for column top stream may be used in a heating process in which the reboiler 103 is used before the raw material 110 flows into the divided-wall distillation column 100, or may be used as a heat source in a vaporizer, a stripping column or an isomer column used in a process of preparing an octanol. Also, energy-saving and cost-cutting effects by the piping system and the heat exchanger 400 for product stream, both of which are formed to exchange heat with the raw material 110, may be achieved, as described above. In addition, when the divided-wall distillation column 100 includes the heat exchanger for column top stream, an effect of cutting the cost consumed in a condensation process in which the condenser 102 is used may be further achieved by reducing the quantity of cooling water used in the condensation process before some of the low boiling point stream in the divided-wall distillation column 100 is refluxed to the column top region 104 of the divided-wall distillation column 100, as described above. In this case, the low boiling point stream refluxed to the distillation column 100 after the heat exchange is completed may have a reflux ratio of 1 to 100. In a thermodynamic aspect, the reflux ratio of the low boiling point stream may be preferably in a range of 5 to 70, more preferably 7.2 to 16.5. When the raw material whose heat exchange is completed by means of the heat exchanger 400 for product stream flows into the distillation column, and then flows out from the column top region at a temperature of 100 to 120° C., the energy consumed to reflux the column top stream refluxed to the distillation column 100 in the column top stream 120 which has a temperature of 40 to 120° C. and exchanges heat by means of the heat exchanger 300 for column top stream may be minimized, and some of the column top stream may be simultaneously produced as a high-purity product by adjusting the reflux ratio in a range of 100 or less, preferably 70 or less, and most preferably 16.5 or less, as described above. In this case, 2-ethylhexanol having a high purity, for example, a purity of 99.0% or more, may also be produced from the product stream 140 by adjusting the reflux ratio in a range of 5 to 70, preferably 7.2 to 16.5.

Although not shown, the exemplary device for preparing an alkanol according to one exemplary embodiment of the present application may also include the heat exchanger 310 configured to preheat a raw material for column top stream, and the heat exchanger 400 for product stream. For example, the raw material 110 flowing into the divided-wall distillation column 100 may be preheated when the low boiling point stream exchanges heat with the low-temperature raw material 110 flowing into the divided-wall distillation column 100 using the heat exchanger 310 configured to preheat a raw material for column top stream. When the raw material 110 is not sufficiently preheated, the raw material may be further preheated by means of the heat exchanger 400 for product stream. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a condensation process in which the condenser 102 is used may be cut by reducing the quantity of cooling water used in the condensation process before the low boiling point stream in the divided-wall distillation column 100 is refluxed to the column top region 104 of the divided-wall distillation column 100. According to one exemplary embodiment, the temperature of the product stream may be regulated so that a difference in temperature ($\Delta T_{min}$) between the product stream 140 and the raw material preheated by means of the heat exchanger 310 configured to preheat a raw material for column top stream is greater than or equal to 5° C. For example, the difference in temperature ($\Delta T_{min}$) may be regulated by pressurizing or depressurizing the pipe through which the product stream flows. In this case, the low boiling point stream refluxed to the distillation column 100 after the heat exchange is completed may also have a reflux ratio of 1 to 100. In a thermodynamic aspect, the reflux ratio of the low boiling point stream may be preferably in a range of 5 to 70, more preferably 6.8 to 16.1. When the raw material whose heat exchange is completed by means of the heat exchanger 400 for product stream flows into the distillation column, and then flows out from the column top region 104 at a temperature of 100 to 120° C., the energy consumed to reflux the column top stream 120, which exchanges heat by means of the heat exchanger 310 for column top stream and is refluxed to the distillation column 100 at a temperature of 40 to 120° C., may be minimized, and some of the column top stream may be simultaneously produced as a high-purity product by adjusting the reflux ratio in a range of 100 or less, preferably 16.1 or less, as described above.

According to still another exemplary embodiment of the present application, the heat exchanger may be a heat exchanger for column bottom stream, and, according to one exemplary embodiment, may be a heat exchanger configured to preheat a raw material.

Figure 5:
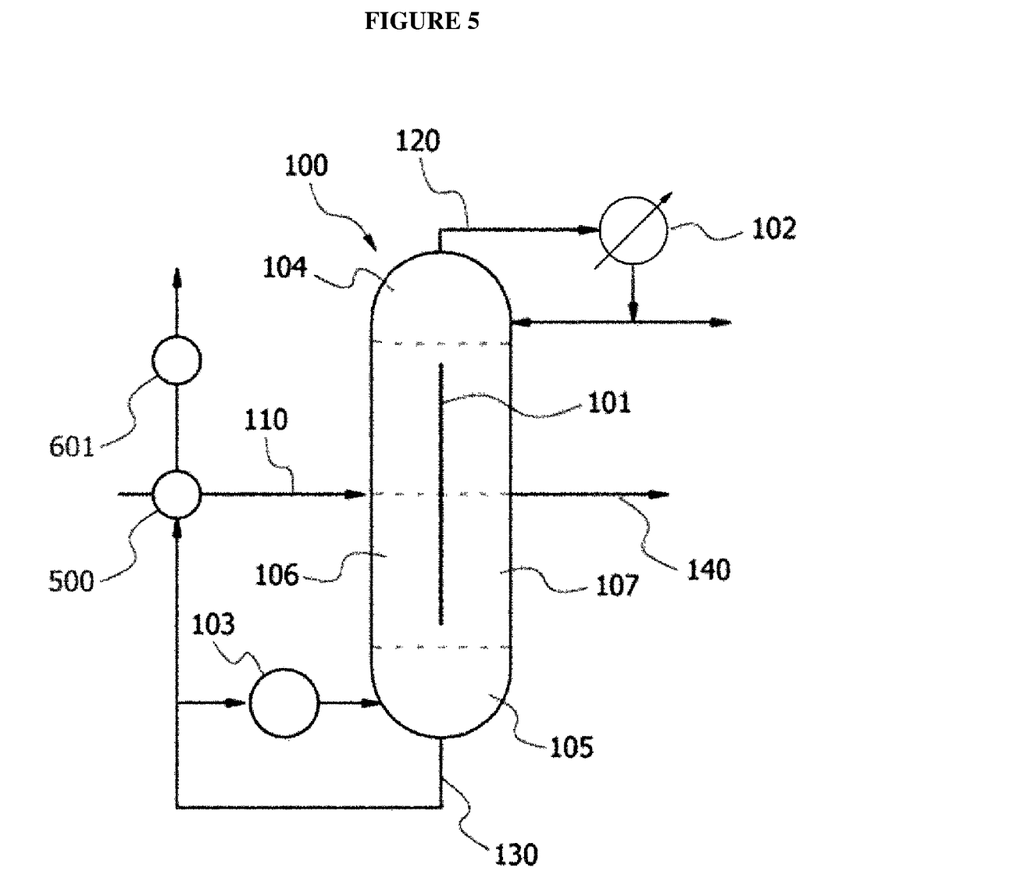

FIG. 5 is a diagram showing an exemplary preparing device according to a fourth exemplary embodiment of the present application.

As shown in FIG. 5, in the exemplary preparing device, some of the high boiling point stream flowing out from the column bottom region 105 is refluxed to the column bottom region 105 through the reboiler, and some or all of the rest of the high boiling point stream may flows through the pipe so that the high boiling point stream can exchange heat with the raw material 110 flowing into the divided-wall distillation column 100 in a heat exchanger 500 configured to preheat a raw material for column bottom stream, and the high boiling point stream may be produced as an article while sequentially passing through a cooler 601. As the high boiling point stream passes through the heat exchanger 500 configured to preheat a raw material for column bottom stream, some or all of the high boiling point stream flowing out from the column bottom region 105 may exchange heat with the raw material 110 flowing into the raw material feed region 106 so as to preheat the raw material 110. For example, the raw material 110 flowing into the divided-wall distillation column 100 may be preheated when the high boiling point stream exchanges heat with the low-temperature raw material 110 flowing into the divided-wall distillation column 100 using the heat exchanger 500 configured to preheat a raw material for column bottom stream. Therefore, the cost spent in a condensation process in which the condenser 102 is used may be cut by reducing the quantity of cooling water used in the condensation process before the low boiling point stream in the divided-wall distillation column 100, that is, the column top stream 120, is refluxed to the column top region 104 of the divided-wall distillation column 100. Further, the cost spent in a cooling process in which the cooler 601 is used may be cut by reducing the quantity of cooling water used in the cooling process before the high boiling point stream is produced as a product. In this case, the low boiling point stream refluxed to the distillation column 100 after the heat exchange is completed, the column top stream 120 may also have a reflux ratio of 1 to 100. In a thermodynamic aspect, the reflux ratio of the column top stream 120 may be preferably in a range of 5 to 70, more preferably 16.6 to 19.8. When the reflux ratio of the column top stream 120 is adjusted in a range of 100 or less, preferably 70 or less, and most preferably, 19.8 or less, the energy consumed to cool the column bottom stream 130 flowing into a storage tank in the column bottom stream 130 which has a temperature of 40 to 100° C. and exchanges heat with the raw material by means of the heat exchanger 500 for column bottom stream may be minimized, and some of the column top stream 120 may be produced as a high-purity product at the same time. In this case, 2-ethylhexanol having a high purity, for example, a purity of 99.0% or more, may also be produced from the product stream 140 by adjusting the reflux ratio in a range of 5 to 70, preferably 16.6 to 19.8.

According to one exemplary embodiment, although not shown, the preparing device may include the heat exchanger 500 configured to preheat a raw material for column bottom stream, and the heat exchanger 400 for product stream. For example, the raw material 110 flowing into the divided-wall distillation column 100 may be preheated when the product stream exchanges heat with the raw material 110 flowing into the low-temperature divided-wall distillation column 100 using the heat exchanger 400 configured to preheat a raw material for product stream. When the raw material 110 is not sufficiently preheated, the raw material may be further preheated by means of the heat exchanger 500 for column bottom stream. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a condensation process in which the condenser 102 is used may be cut by reducing the quantity of cooling water used in the condensation process before the low boiling point stream in the divided-wall distillation column 100 is refluxed to the column top region 104 of the divided-wall distillation column 100. According to one exemplary embodiment, the temperature of the column bottom stream 130 may be regulated so that a difference in temperature ($\Delta T_{min}$) between the column bottom stream and the raw material preheated through the heat exchanger 400 configured to preheat a raw material for product stream is greater than or equal to 5° C. For example, the difference in temperature ($\Delta T_{min}$) may be regulated by pressurizing or depressurizing the pipe through which the column bottom stream 130 flows. In this case, the low boiling point stream refluxed to the distillation column 100 after the heat exchange is completed, that is, the column top stream 120, may also have a reflux ratio of 1 to 100. In a thermodynamic aspect, the reflux ratio of the low boiling point stream may be preferably in a range of 5 to 70, more preferably 12.1 to 17.0. In this case, 2-ethylhexanol having a high purity, for example, a purity of 99.0% or more, may also be produced from the product stream 140 by adjusting the reflux ratio in a range of 100 or less, preferably 17.0 or less, as described above.

Although not shown, according to one exemplary embodiment, the preparing device may also include the heat exchanger 310 configured to preheat a raw material for column top stream, and the heat exchanger 500 configured to preheat a raw material for column bottom stream. For example, the raw material 110 flowing into the divided-wall distillation column 100 may be preheated when the column top stream 120 in the divided-wall distillation column exchanges heat with the raw material 110 flowing into the low-temperature divided-wall distillation column 100 using the heat exchanger 310 configured to preheat a raw material for column top stream. When the raw material 110 is not sufficiently preheated, the raw material may be further preheated by means of the heat exchanger 500 for column bottom stream.

Still another exemplary embodiment of the present application provides a device for preparing an alkanol, which includes a divided-wall distillation column provided with a condenser, a reboiler, a heat exchanger configured to produce steam for column top stream, a heat exchanger configured to preheat a raw material, and a divided wall.

Figure 6:
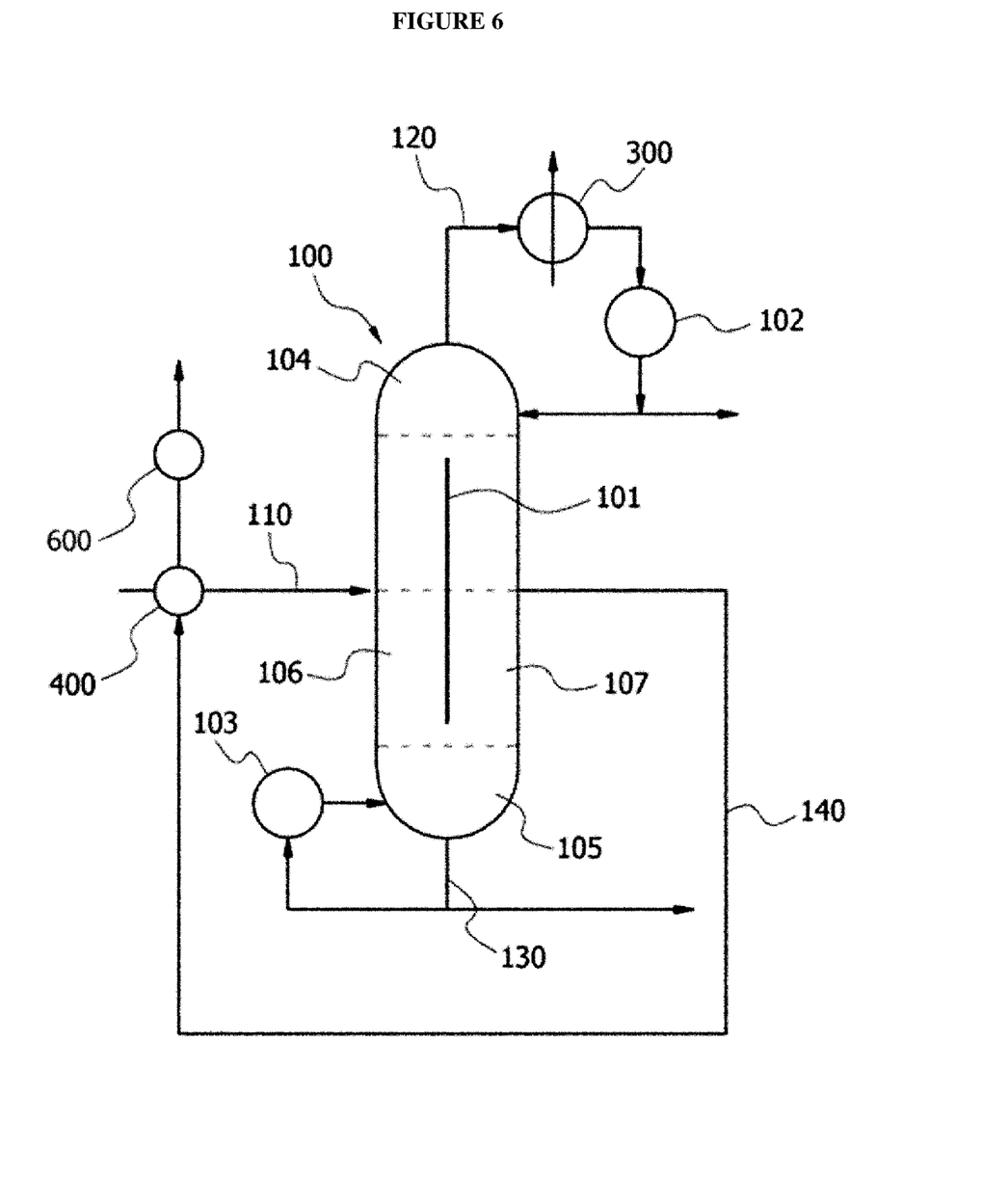

FIG. 6 is a diagram showing an exemplary device for preparing an alkanol according to a fifth exemplary embodiment of the present application.

As shown in FIG. 6, the device for preparing an alkanol according to one exemplary embodiment of the present application may include a divided-wall distillation column 100 which is provided with a condenser 102, a reboiler 103, and a divided wall 101, and is divided into a raw material feed region 106, a product outflow region 107, a column top region 104, and a column bottom region 105. Also, the divided-wall distillation column 100 may include a heat exchanger 300 for column top stream, and a heat exchanger configured to preheat a raw material. As described above, the raw material 110 including an octanol, for example, 2-ethylhexanol, may flow in the raw material feed region 106 of the divided-wall distillation column 100, and the raw material 110 flowing into the material feed region 106 may be separated into a product stream 140, a high boiling point stream, and a low boiling point stream to flow out therefrom. In the foregoing, the high boiling point stream may also flow out from the column bottom region 105, and some of the high boiling point stream may be refluxed to the distillation column 100 through the reboiler 103. In the foregoing, the low boiling point stream may flow out from the column top region 104, and pass through the condenser 102, and some of the stream passing through the condenser 102 may be refluxed to the distillation column 100.

According to one exemplary embodiment, the heat exchanger 300 for column top stream may be a heat exchanger configured to produce steam. For example, as some or all of the low boiling point stream pass through the heat exchanger 300 for column top stream, the low boiling point stream in the divided-wall distillation column 100 may exchange heat with water so as to produce steam, as described above. For example, the steam produced in the heat exchanger 300 for column top stream may be used in a heating process in which the heater is used before the raw material 110 flows into the divided-wall distillation column 100, or may be used as a heat source in a vaporizer, a stripping column or an isomer column used in a process of preparing an octanol. Also, energy-saving and cost-cutting effects by the piping system and the heat exchanger 400 for product stream, both of which are formed to perform the heat exchange with the raw material 110, may be achieved, as described above. In addition, when the divided-wall distillation column 100 includes the heat exchanger 300 for column top stream, an effect of cutting the cost consumed in a condensation process in which the condenser 102 is used may be further achieved by reducing the quantity of cooling water used in the condensation process before some of the low boiling point stream in the divided-wall distillation column 100 is refluxed to the column top region 104 of the divided-wall distillation column 100, as described above.

Also, the divided-wall distillation column includes a heat exchanger configured to preheat a raw material. According to one exemplary embodiment, in the heat exchanger configured to preheat a raw material, some or all of the column bottom stream 130 or the product stream 140 exchanges heat with the raw material flowing into the raw material feed region so as to heat the raw material.

According to one exemplary embodiment of the present application, the heat exchanger configured to preheat a raw material may be a heat exchanger 400 for product stream, as shown in FIG. 6. In the foregoing, the heat exchanger 400 for product stream may be arranged to be directly or indirectly coupled to a pipe through which the product stream 140 in the preparing device flows. In a thermodynamic aspect, the heat exchanger 400 for product stream may be preferably directly coupled to the pipe through which the product stream 140 in the distillation column 100 flows.

As the product stream 140 in the divided-wall distillation column 100 passes through the heat exchanger 400 for product stream, heat may be applied to the heat exchanger 400 for product stream by means of the heat exchanger 400 for product stream coupled to the pipe as described above. As described above, the raw material 110 flowing into the divided-wall distillation column 100 may be preheated to raise the temperature of the raw material 110 when the product stream 140 exchanges heat with the low-temperature raw material 110 flowing into the divided-wall distillation column 100. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a cooling process in which the cooler 600 is used may be cut by reducing the quantity of cooling water used in the cooling process before the stream including the octanol is produced as a product.

In this case, the column top stream refluxed to the distillation column 100 after the heat exchange is completed may also have a reflux ratio of 1 to 100. In a thermodynamic aspect, the reflux ratio of the column top stream may be preferably in a range of 5 to 70, more preferably 7.2 to 16.5. When the raw material whose heat exchange is completed by means of the heat exchanger for product stream flows into the distillation column, and then flows out from the column top region at a temperature of 100 to 120° C., the energy consumed to reflux the column top stream 120, which exchanges heat by means of the heat exchanger for column top stream and is refluxed to the distillation column 100 at a temperature of 40 to 120° C., may be minimized, and some of the column top stream 120 may be simultaneously produced as a high-purity product by adjusting the reflux ratio in a range of 100 or less, preferably 16.5 or less, as described above. In this case, 2-ethylhexanol having a high purity, for example, a purity of 99.0% or more, may also be produced from the product stream 140 by adjusting the reflux ratio in a range of 5 to 70, preferably 7.2 to 16.5.

According to yet another exemplary embodiment of the present application, the divided-wall distillation column 100 may also include the heat exchanger 300 for column top stream, and a heat exchanger configured to preheat a raw material. According to one exemplary embodiment, the heat exchanger configured to preheat a raw material may be a heat exchanger for column bottom stream.

Figure 7:
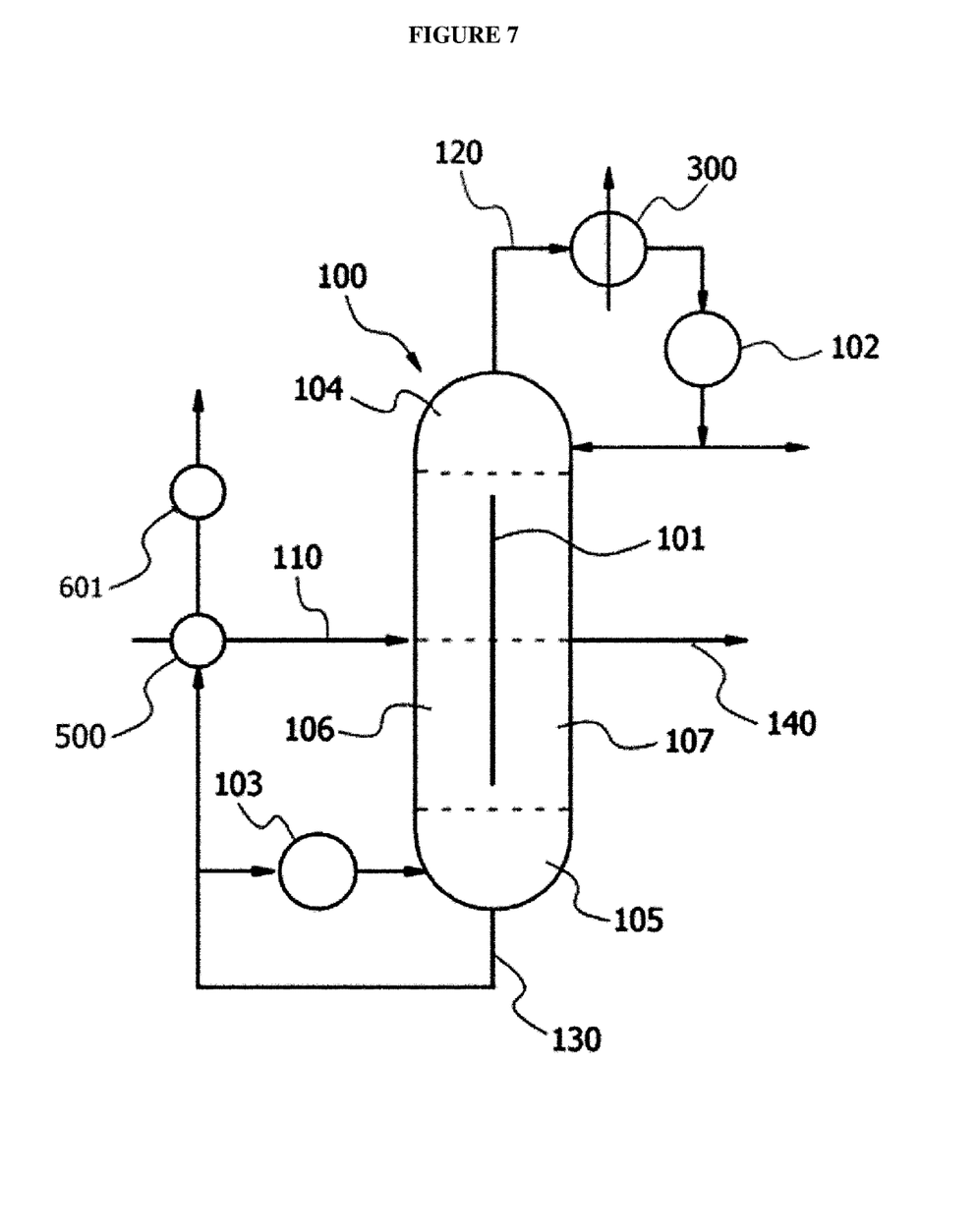

FIG. 7 is a diagram showing an exemplary device for preparing an alkanol according to a sixth exemplary embodiment of the present application.

In the foregoing, the heat exchanger 500 for column bottom stream may be arranged to be directly or indirectly coupled to a pipe through which the column bottom stream 130 in the preparing device flows. In a thermodynamic aspect, the heat exchanger 500 for column bottom stream may be preferably directly coupled to the pipe through which the column bottom stream 130 in the distillation column 100 flows.

As the column bottom stream 130 in the divided-wall distillation column 100 passes through the heat exchanger 500 for column bottom stream, heat may be applied to the heat exchanger 500 for column bottom stream by means of the heat exchanger 500 for column bottom stream coupled to the pipe as described above. As described above, the raw material 110 flowing into the divided-wall distillation column 100 may be preheated to raise the temperature of the raw material 110 when the column bottom stream 130 exchanges heat with the raw material 110 flowing into the divided-wall distillation column 100. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a cooling process in which the cooler 601 is used may be cut by reducing the quantity of cooling water used in the cooling process before the high boiling point stream is produced as a product. In this case, the column top stream 120 refluxed to the distillation column 100 after the heat exchange is completed may also have a reflux ratio of 1 to 100. In a thermodynamic aspect, the reflux ratio of the column top stream 120 may be preferably in a range of 5 to 70, more preferably 8.1 to 17.1. In this case, 2-ethylhexanol having a high purity, for example, a purity of 99.0% or more, may also be produced from the product stream 140 by adjusting the reflux ratio in a range of 100 or less, preferably 70 or less, and most preferably, 17.1 or less, as described above.

Another aspect of the present application provides a method of preparing an alkanol. For example, the preparing method may be performed using the above-described device for preparing an alkanol. The exemplary method may include allowing the raw material 110 including a compound represented by the following Formula 1, for example, an octanol such as 2-ethylhexanol, to flow into the divided-wall distillation column 100, and distilling the raw material 110 flowing into the divided-wall distillation column 100 and separating the raw material into a product stream 140, a column bottom stream 130, and a column top stream 120 to flow out therefrom.

[Formula 1]

In Formula 1, R represents an alkyl group.

According to one exemplary embodiment, in the preparing method, some or all of the column top stream 120 may exchange heat with raw material 110 flowing into the distillation column 100 or water outside the distillation column 100.

For example, the raw material 110 flowing into the divided-wall distillation column 100 may be preheated when some or all of the column top stream 120 exchanges heat with the raw material 110 flowing into the low-temperature divided-wall distillation column 100. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a condensation process in which the condenser 102 is used may be cut by reducing the quantity of cooling water used in the condensation process before the column top stream 120 in the divided-wall distillation column 100 is refluxed to the column top region 104 of the divided-wall distillation column 100. According to one exemplary embodiment, the reflux ratio of the column top stream 120 refluxed to the distillation column 100 after the heat exchange is completed may be adjusted in a range of 1 to 100. In a thermodynamic aspect, the reflux ratio of the column top stream 120 may be preferably adjusted in a range of 5 to 70, more preferably 8.4 to 17.3.

Also, a high-temperature steam may be produced when some or all of the column top stream 120 exchanges heat with water outside the distillation column 100. For example, the produced high-temperature steam may be used as a heat source in a vaporizer, a stripping column or an isomer column used in a process of preparing an octanol. According to one exemplary embodiment, the reflux ratio of the column top stream 120 refluxed to the distillation column 100 after the heat exchange is completed may be adjusted in a range of 1 to 100. In a thermodynamic aspect, the reflux ratio of the column top stream 120 may be preferably adjusted in a range of 5 to 70, more preferably 18.5 to 25.5.

According to one exemplary embodiment, in the preparing method, some or all of the product stream 140 or the column bottom stream may also further exchange heat with the raw material 110 flowing into the distillation column 100.

For example, in the preparing method, some or all of the column top stream 120 may exchange heat with water outside the distillation column 100, and some or all of the product stream 140 may exchange heat with the raw material 110 flowing into the distillation column 100. In this case, the reflux ratio of the column top stream 120 refluxed to the distillation column 100 after the heat exchange is completed may be adjusted in a range of 1 to 100. In a thermodynamic aspect, the reflux ratio of the column top stream may be preferably adjusted in a range of 5 to 70, more preferably 7.2 to 16.5.

According to one exemplary embodiment, some or all of the column top stream 120 and some or all of the product stream 140 may exchange heat with the raw material 110 flowing into the distillation column 100. In this case, the reflux ratio of the column top stream 120 refluxed to the distillation column 100 after the heat exchange is completed may be adjusted in a range of 1 to 100. In a thermodynamic aspect, the reflux ratio of the column top stream 120 may be preferably adjusted in a range of 5 to 70, more preferably 8.4 to 17.3.

In the preparing method, some or all of the column top stream 120 may also exchange heat with water outside the distillation column 100, and some or all of the column bottom stream may exchange heat with the raw material 110 flowing into the distillation column 100. In this case, the reflux ratio of the column top stream 120 refluxed to the distillation column 100 after the heat exchange is completed may be adjusted in a range of 1 to 100. In a thermodynamic aspect, the reflux ratio of the column top stream 120 may be preferably adjusted in a range of 5 to 70, more preferably 8.1 to 17.1.

According to one exemplary embodiment, some or all of the column top stream 120 and some or all of the column bottom stream 130 may exchange heat with the raw material 110 flowing into the distillation column 100. In this case, the reflux ratio of the column top stream 120 refluxed to the distillation column 100 after the heat exchange is completed may be adjusted in a range of 1 to 100. In a thermodynamic aspect, the reflux ratio of the column top stream 120 may be preferably adjusted in a range of 5 to 70, more preferably 9.1 to 17.6.

According to one exemplary embodiment, some or all of the product stream 140 and some or all of the column bottom stream 130 may also exchange heat with the raw material 110 flowing into the distillation column 100. In this case, the reflux ratio of the column top stream 120 refluxed to the distillation column 100 after the heat exchange is completed may be adjusted in a range of 1 to 100. In a thermodynamic aspect, the reflux ratio of the column top stream 120 may be preferably adjusted in a range of 5 to 70, more preferably 12.1 to 17.0.

Also, some or all of the column top stream 120 may exchange heat with water outside the distillation column 100, and some or all of the column top stream 120 and some or all of the product stream 140 may exchange heat with the raw material 110 flowing into the distillation column 100. In this case, the reflux ratio of the column top stream 120 refluxed to the distillation column 100 after the heat exchange is completed may be adjusted in a range of 1 to 100. In a thermodynamic aspect, the reflux ratio of the column top stream 120 may be preferably adjusted in a range of 5 to 70, more preferably 7.2 to 16.5.

When some or all of the column bottom stream 130 and/or the product stream 140 further exchange heat with the raw material 110 flowing into the low-temperature divided-wall distillation column 100, as described above, the energy-saving and cost-cutting effects may be achieved when some or all of the column top stream 120 exchanges heat with the raw material 110 flowing into the distillation column 100 or water outside the distillation column 100. In addition, the raw material 110 flowing into the divided-wall distillation column 100 may be preheated to raise the temperature of the raw material 110. Therefore, the energy consumed in a heater configured to raise a temperature of the raw material 110 flowing into the divided-wall distillation column 100, or a reboiler 103 configured to heat the column bottom stream 130 discharged from the column bottom region 105 of the divided-wall distillation column 100 may be reduced. Further, the cost spent in a cooling process in which the cooler 600 or 601 is used may be cut by reducing the quantity of cooling water used in the cooling process before the middle boiling point stream and/or the high boiling point stream including the octanol is produced as a product.

According to one exemplary embodiment, in the preparing method, the raw material 110 flowing into the divided-wall distillation column 100 before the raw material 110 exchanges heat with the column top stream 120 or the product stream 140 in the divided-wall distillation column 100 may be maintained at a temperature of 30° C. to 50° C., and the raw material 110 flowing into the divided-wall distillation column 100 after the raw material 110 exchanges heat with the column top stream 120 or the product stream 140 in the divided-wall distillation column 100 may be maintained at a temperature of 60° C. to 130° C.

According to one exemplary embodiment, in the method of preparing an alkanol according to the present application, a separation process may be performed, for example, while maintaining an upper portion of the divided-wall distillation column 100 at an operating pressure of 0.01 Kg/cm$^2$ to 10 Kg/cm$^2$. Also, in the preparing method, the separation process may be performed, for example, while maintaining a lower portion of the divided-wall distillation column 100 at an operating pressure of 0.3 Kg/cm$^2$ to 11 Kg/cm$^2$.

Advantageous Effects

According to one exemplary embodiment of the present application, energy saving can be promoted upon the manufacture of an alkanol by reducing the quantity of steam used in a reboiler of the device or the quantity of cooling water used in a condenser and a cooler, and the steam generated from a heat exchanger for column top stream can be used in a variety of fields. Also, a high-purity alkanol can be prepared according to one exemplary embodiment of the present application.

BEST MODE

Hereinafter, the present application will be described in further detail with reference to Examples according to the present application and Comparative Example not according to the present application, but the scope of the present application is not limited to the following Examples.

Example 1

An octanol was prepared using a divided-wall distillation column, as shown in FIG. 2. Specifically, a process of introducing a raw material including 2-ethylhexanol into the divided-wall distillation column and separating the raw material was performed. In this case, the conditions of such a process were set so that the operating pressure and operating temperature of a lower portion of the divided-wall distillation column were approximately 0.8 Kg/cm$^2$ and approximately 160° C., respectively, and the operating pressure and operating temperature of an upper portion of the divided-wall distillation column were approximately 0.3 Kg/cm$^2$ and approximately 95° C., respectively. Also, some of a high boiling point stream discharged from a column bottom region of the divided-wall distillation column was refluxed to the divided-wall distillation column through a reboiler. In addition, some of a low boiling point stream and water discharged from a column top region of the divided-wall distillation column was re-introduced into the divided-wall distillation column through a condenser, and the rest of the low boiling point stream was separated as a product. In this case, low boiling point components and water discharged from the column top region of the divided-wall distillation column passed through a heat exchanger configured to produce steam for column top stream before the low boiling point components and water passed through the condenser. In this case, the reflux ratio of the column top stream in the divided-wall distillation column was set so that the column top stream had a reflux ratio of 18.5 to 25.5.

Example 2

An octanol was refined in the same manner as in Example 1, except that the low boiling point components and water discharged from the column top region of the divided-wall distillation column exchanged heat with a raw material introduced into the divided-wall distillation column, using a heat exchanger configured to preheat a raw material for column top stream, before the low boiling point components and water passed through the condenser, as shown in FIG. 3. In this case, the reflux ratio of the column top stream in the divided-wall distillation column was set so that the column top stream had a reflux ratio of 8.4 to 17.3.

Example 3

An octanol was refined in the same manner as in Example 1, except that a product stream discharged from a product outflow region of the divided-wall distillation column exchanged heat with the raw material introduced into the divided-wall distillation column, using a heat exchanger configured to preheat a raw material for product stream, before the product stream flowed in a storage tank through a cooler, as shown in FIG. 4. In this case, the reflux ratio of the column top stream in the divided-wall distillation column was set so that the column top stream had a reflux ratio of 15.2 to 18.5.

Example 4

An octanol was refined in the same manner as in Example 1, except that a portion of a column bottom stream discharged from a column bottom region of the divided-wall distillation column was refluxed to the column bottom region through the reboiler, and the rest of the column bottom stream exchanged heat with the raw material introduced into the divided-wall distillation column using a heat exchanger configured to preheat a raw material for column bottom stream, as shown in FIG. 5. In this case, the reflux ratio of the column top stream in the divided-wall distillation column was set so that the column top stream had a reflux ratio of 16.6 to 19.8.

Example 5

An octanol was refined in the same manner as in Example 1, except that a product stream of octanol discharged from the product outflow region of the divided-wall distillation column exchanged heat with the raw material introduced into the divided-wall distillation column, using the heat exchanger configured to preheat a raw material for product stream, before the product stream of octanol passed through the cooler, and the low boiling point components and water discharged from the column top region of the divided-wall distillation column passed through the heat exchanger configured to produce steam for column top stream before the low boiling point components and water passed through the condenser, as shown in FIG. 6. In this case, the reflux ratio of the column top stream in the divided-wall distillation column was set so that the column top stream had a reflux ratio of 7.2 to 16.5.

Example 6

An octanol was refined in the same manner as in Example 1, except that some of the column bottom stream discharged from the column bottom region of the divided-wall distillation column was refluxed to the column bottom region through the reboiler, the rest of the column bottom stream exchanged heat with the raw material introduced into the divided-wall distillation column using the heat exchanger configured to preheat a raw material for column bottom stream, and the low boiling point components and water discharged from the column top region of the divided-wall distillation column passed through the heat exchanger configured to produce steam for column top stream before the low boiling point components and water passed through the condenser, as shown in FIG. 7. In this case, the reflux ratio of the column top stream in the divided-wall distillation column was set so that the column top stream had a reflux ratio of 8.1 to 17.1.

Comparative Example 1

Figure 8:
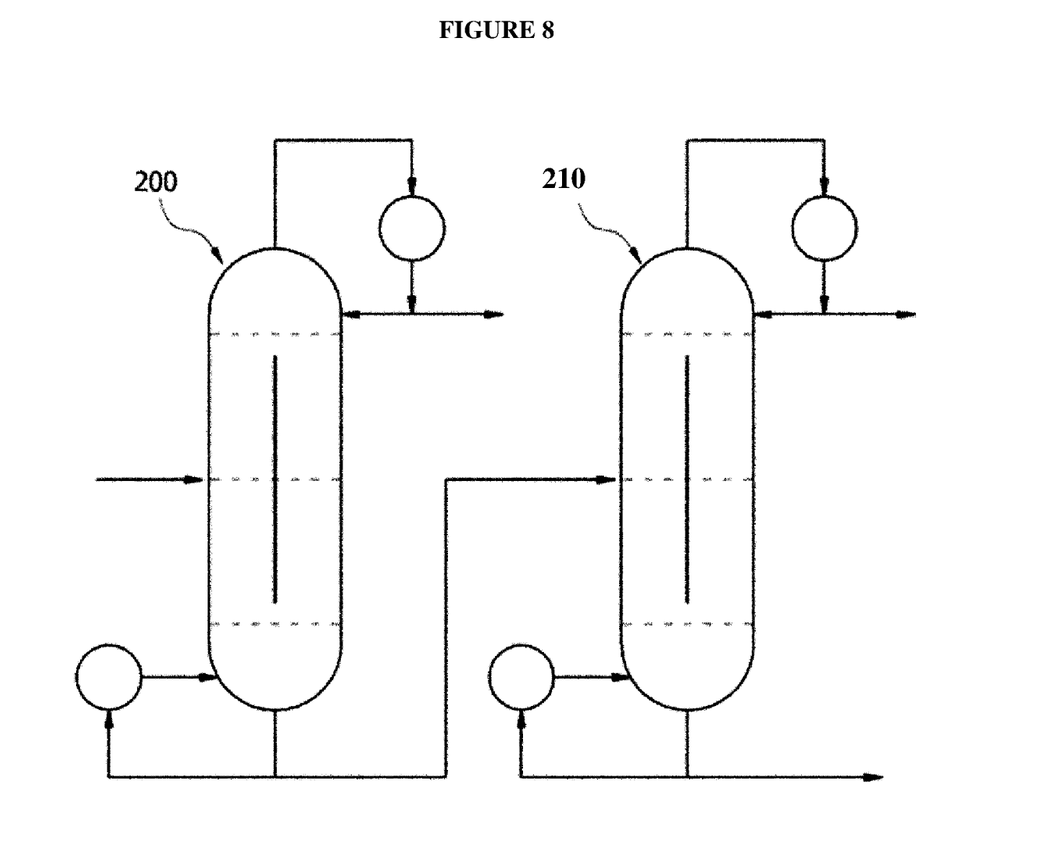
FIG. 8 is a diagram showing a device for preparing an alkanol used in Comparative Example 1.

An octanol was refined using a distillation column assembly in which general-type distillation columns were sequentially connected as shown in FIG. 8. A stream discharged from a column top region of a first general-type distillation column 200 passed through a condenser, and some of the stream was then refluxed to the first general-type distillation column, and the rest of the stream was produced as a product. A stream discharged from a column bottom region of the first general-type distillation column 200 passed through a reboiler, and some of the stream was then refluxed to the first general-type distillation column, and the rest of the stream flowed in a second general-type distillation column 210. A stream discharged from a column top region of the second distillation column 210 passed through the condenser, and some of the stream was then refluxed to the second distillation column 210, and the rest of the stream was produced as an octanol. A stream discharged from a column bottom region of the second distillation column 210 passed through the reboiler, and some of the stream was then refluxed to the second distillation column 210, and the rest of the stream was produced as a product. In this case, the reflux ratios of the column top streams of the first distillation column 200 and the second distillation column 210 were set so that the column top streams of the first distillation column 200 and the second distillation column 210 had a reflux ratio of 10 to 20 and 1 to 10, respectively.

Measurement of Energy Used

When an octanol was separated and refined using each of the preparing devices used in Examples 1 to 6 and Comparative Example 1, the energy used was measured. The results are listed in the following Table 1.

TABLE 1

| | Energy consumed in each column (gal/hr) | Reflux ratio of column top stream in each column | Total quantity of energy consumed (gal/hr) | Reduction in energy (%) |
|---|---|---|---|---|
| Example 1 | DWC | 3.36 | 18.5 to 25.5 | 3.36 | 55.5 |
| Example 2 | DWC | 3.52 | 8.4 to 17.3 | 3.52 | 53.4 |
| Example 3 | DWC | 4.21 | 15.2 to 18.5 | 4.21 | 44.1 |
| Example 4 | DWC | 4.58 | 16.6 to 19.8 | 4.58 | 39.3 |
| Example 5 | DWC | 2.98 | 7.2 to 16.5 | 2.98 | 60.5 |
| Example 6 | DWC | 3.12 | 8.1 to 17.1 | 3.12 | 58.7 |
| Comparative Example 1 | General-type distillation column | 3.91 | 10 to 20 | 7.55 | — |
| | general-type distillation column | 3.64 | 1 to 10 | | |

As listed in Table 1, it was revealed that the preparing devices used in Examples 1 to 6 of the present application had an energy-saving effect up to 60.5% when the octanol was separated using the preparing devices, compared to the preparing device of Comparative Example 1.

The invention claimed is:

1. A device, comprising:
a distillation column provided with a condenser, a reboiler, a heat exchanger, and a divided wall,
wherein the distillation column is divided into a raw material feed region, a product outflow region, a column top region, and a column bottom region,
a raw material comprising a compound represented by the following Formula 1 flows into the raw material feed region, and the raw material flowing into the raw material feed region is separated into a product stream, a column bottom stream and a column top stream to flow out therefrom,
the column bottom stream flows out from the column bottom region, and some of the column bottom stream is refluxed to the distillation column through the reboiler,
the column top stream flows out from the column top region and passes through the condenser, and some of the column top stream passing through the condenser is refluxed to the distillation column,
the product stream flows out from the product outflow region, and
some or all of at least one stream selected from the column top stream, the bottom stream, and the product stream exchanges heat while passing through the heat exchanger:

$$R\text{---}OH \qquad \text{[Formula 1]}$$

wherein R represents an alkyl group, and
wherein the column top stream has a reflux ratio of 5 to 70.

2. The device of claim 1, wherein the compound of Formula 1 is octanol.

3. The device of claim 1, wherein the compound of Formula 1 is 2-ethylhexanol.

4. The device of claim 1, wherein the heat exchanger is a heat exchanger configured to produce steam, and wherein the heat exchanger is arranged in a stage prior to the condenser and configured such that some or all of the column top stream flowing out from the column top region exchanges heat with water to produce steam.

5. The device of claim 1, wherein the heat exchanger is a heat exchanger configured to preheat a raw material, and wherein the heat exchanger is arranged in a stage prior to the condenser and configured such that some or all of the column top stream flowing out from the column top region exchanges heat with the raw material flowing into the raw material feed region to heat the raw material.

6. The device of claim 1, wherein the heat exchanger is a heat exchanger configured to preheat a raw material, and wherein the heat exchanger is arranged in a stage prior to the raw material feed region and configured such that some or all of the product stream flowing out from the product outflow region exchanges heat with the raw material flowing into the raw material feed region to heat the raw material.

7. The device of claim 1, wherein the heat exchanger is a heat exchanger configured to preheat a raw material, and wherein the heat exchanger is arranged in a stage prior to the raw material feed region and configured such that some or all of the column bottom stream flowing out from the column bottom region exchanges heat with the raw material flowing into the raw material feed region to heat the raw material.

8. A device, comprising:
   a distillation column provided with a condenser, a reboiler, a heat exchanger configured to produce steam, a heat exchanger configured to preheat a raw material, and a divided wall,
   wherein the distillation column is divided into a raw material feed region, a product outflow region, a column top region, and a column bottom region,
   a raw material comprising a compound represented by the following Formula 1 flows into the raw material feed region, and the raw material flowing into the raw material feed region is divided into a product stream, a column bottom stream and a column top stream to flow out therefrom,
   the column bottom stream flows out from the bottom region, and some of the column bottom stream is refluxed to the distillation column through the reboiler,
   the column top stream flows out from the column top region, and sequentially passes through the heat exchanger configured to produce steam, and the condenser, and some of the column top stream passing through the condenser is refluxed to the distillation column,
   the product stream flows out from the product outflow region,
   some or all of the column top stream exchanges heat with water in the heat exchanger configured to produce steam so as to produce steam, and
   some or all of the bottom stream or product stream exchanges heat with the raw material flowing into the raw material feed region in the heat exchanger configured to preheat a raw material so as to heat the raw material:

R—OH  [Formula 1]

wherein R represents an alkyl group, and
   wherein the column top stream has a reflux ratio of 5 to 70.

9. The device of claim 8, wherein the compound of Formula 1 is an octanol.

10. The device of claim 8, wherein the compound of Formula 1 is 2-ethylhexanol.

11. The device of claim 8, wherein the heat exchanger configured to preheat a raw material is a heat exchanger configured to preheat a raw material, and wherein some or all of the column bottom stream flowing out from the column bottom region exchanges heat with the raw material flowing into the raw material feed region so as to heat the raw material.

12. The device of claim 8, wherein the heat exchanger configured to preheat a raw material is a heat exchanger configured to preheat a raw material, and wherein some or all of the product stream flowing out from the product outflow region exchanges heat with the raw material flowing into the raw material feed region so as to heat the raw material.

13. A method comprising:
   allowing a raw material comprising a compound represented by the following Formula 1 to flow into a divided-wall distillation column; and
   distilling the raw material flowing into the divided-wall distillation column and separating the raw material into a product stream, a column bottom stream and a column top stream to flow out therefrom,
   wherein some or all of the column top stream exchanges heat with the raw material flowing into the distillation column or water outside the distillation column:

R—OH  [Formula 1]

wherein R represents an alkyl group, and
   wherein the column top stream has a reflux ratio of 5 to 70.

14. The method of claim 13, wherein the compound of Formula 1 is an octanol.

15. The method of claim 13, wherein the compound of Formula 1 is 2-ethylhexanol.

16. The method of claim 13, wherein some or all of the product stream or the column bottom stream further exchanges heat with the raw material flowing into the distillation column.

* * * * *